United States Patent [19]
Sapia et al.

[11] Patent Number: 5,513,531
[45] Date of Patent: May 7, 1996

[54] ULTRASONIC SYSTEM FOR MEASUREMENT OF THIN LAYERS

[75] Inventors: Mark A. Sapia, Canton, Conn.; David S. Leonard, Feeding Hills, Mass.

[73] Assignee: Combustion Engineering, Inc., Windsor, Conn.

[21] Appl. No.: 114,162

[22] Filed: Sep. 1, 1993

[51] Int. Cl.$^6$ .......................... G01N 29/04; G01N 29/00
[52] U.S. Cl. ...................... 73/602; 73/600; 73/618
[58] Field of Search ...................... 73/609, 618, 602, 73/600, 626, 632

[56] References Cited

U.S. PATENT DOCUMENTS

| | | | |
|---|---|---|---|
| 4,052,889 | 10/1977 | Mucciardi et al. | 73/602 |
| 4,459,853 | 7/1984 | Miwa et al. | 73/626 |
| 4,570,486 | 2/1986 | Volkmann | 73/626 |
| 4,853,903 | 9/1989 | Linville, Jr. et al. | 367/46 |
| 5,010,526 | 4/1991 | Linville, Jr. et al. | 367/46 |
| 5,265,217 | 11/1993 | Koukoutsis et al. | 395/2 |
| 5,293,871 | 3/1994 | Reinstein et al. | 73/602 |

OTHER PUBLICATIONS

Bernard Widrow et al., Adaptive Signal Processing, pp. 2, 99, 101–102 (1985).

Primary Examiner—Richard Chilcot
Assistant Examiner—Max H. Noori
Attorney, Agent, or Firm—Ronald P. Kananen

[57] ABSTRACT

To improve and simply ultrasonic measurement of thin layers, an adaptive least-mean-square (LMS) implementation of a Wiener filter is used to deconvolve ultrasonic waveforms. This filter is structured as a finite-impulse-response (FIR) filter and solved using Widrow's adaptive linear combiner. The filter is implemented on a microcomputer with gating features for automated signal peak identification and measurement. The deconvolution process begins by assuming an impulse (the desired response) to a known input (the ultrasonic response). A transfer function is then determined that, when convolved with the response, results in the assumed impulse. The transfer function in this case is a long FIR filter typically requiring up to 128 taps to achieve acceptable results.

18 Claims, 5 Drawing Sheets

ULTRASONIC SYSTEM FOR MEASUREMENT OF THIN LAYERS

FIELD OF THE INVENTION

This invention generally relates to ultrasonic measurement of thin layers. More specifically, it relates to an improved system for measuring thin layers at lower frequency by deconvolving ultrasonic waveforms, such as by using a Wiener filter.

BACKGROUND OF THE INVENTION

In many applications, it is important to detect and accurately measure thin layers. Oxide build-up in fossil boiler tubes, epoxy (carbolene) and other protective coatings (e.g., chrome) on metal surfaces are examples of this need. In fossil boiler tubes, oxide layers form and grow in thickness during normal operation. Measurements of oxide thickness can be used to assess operation and maintenance, or simply to monitor corrosion rates. Therefore, it is desirable to accurately measure the thickness of oxide which is present. The thickness information can then be used to support engineering calculations of heat transfer characteristics and estimates of the remaining life of the tubes.

Typically, the thickness measurement is performed using ultrasonics. In order to improve the resolution of ultrasonic measurement, it is often desired to deconvolve a resulting waveform to recover the "impulse" that was used to generate the response. The "impulse" is the spike or square wave pulse used to excite the transducer. It is a short duration event which, when convolved with the transfer function of the transducer and material, results in a long duration (ringing) response. This long duration response tends to limit the time resolution of separate events, such as a thin oxide layer adhering to a tube wall.

Other systems which have been utilized for oxide measurement typically requires higher frequencies, about 25 MhZ, to achieve a resolution of 6 to 10 mils of oxide thickness. This is a deficiency since more surface preparation is required for the higher frequencies. Also, the results can be ambiguous due to the long duration of the ultrasonic response. Although high frequencies do provide higher resolution, the instrumentation and transducers required by such frequencies are more expensive. Furthermore, it is difficult to obtain quality, low-noise signals.

Another technique to ultrasonically measure thin layers is to look at the waveforms several multiples later in time. This compensates for the lack of resolution by magnifying the time difference between two events. For instance, the first multiple will increase the time difference by a factor of two, the second multiple by a factor of three, and so forth. Unfortunately, attenuation and other effects degrade the signal-to-noise ratio.

An alternate approach is to use a rule-based signal processing scheme that extracts the separate events in the ultrasonic waveform. Various signal features are examined to indicate if and where two separate events are occurring. Unfortunately, the algorithms have proven to be unreliable. The unreliable performance is primarily due to the complex nature of the waveform.

Hence, there is a need to provide an ultrasonic measuring system which utilizes low frequency ultrasound to minimize the amount of surface preparation necessary, yet provides resolution comparable to systems using high frequencies. There is a further need to provide a measuring system which accurately measures thin films, economically and in a reasonable amount of time.

SUMMARY OF THE INVENTION

A general object of this invention is to overcome these and other drawbacks of the prior art, by providing a method and an apparatus for measuring thin films using simplified rule-based signal processing.

It is an object of the invention to provide a method and apparatus in order to deconvolve ultrasonic waveforms to provide high resolution measurements by utilizing an adaptive least-mean-square (LMS) implementation of a Wiener filter.

Another object of this invention is to provide means for structuring a Wiener filter as a finite-impulse response filter (FIR) and solve it using Widrow's adaptive linear combiner.

Another object of this invention is to utilize software to measure a filtered waveform so as to obtain automatically simple and reliable measurement.

These and other objects and advantages are achieved in this invention by providing an apparatus for measuring films located on a test member comprising: a transducer for providing an ultrasonic impulse to the test member; detection means for detecting ultrasonic signals transferred through the test member, said detection means providing data signals indicative of said ultrasonic signals; filtering means for providing a time-based deconvolved filtered waveform based on data signals provided by the detection means; and measurement means for providing a measurement of the test member based on the filtered waveform.

According to another embodiment of the invention the filtering means include processing means for applying a finite-impulse-response (FIR) filter to a waveform based on said data signals provided by the detection means.

According to another embodiment of the invention said FIR filter is a Wiener filter and said processing means calculates Wiener filter coefficients associated with the waveform corresponding to the ultrasonic impulse.

According to another embodiment of the invention there is further provided calibration means for calibrating the apparatus by use of a reference sample substantially similar to the testing sample.

According to another embodiment of the invention said processing means includes a programmable CPU and memory means associated with the programmable CPU.

According to another embodiment of the invention there is further provided a visual display of the measurement of the test member.

According to another embodiment of the invention said display means includes means for providing a visual display of the deconvolved waveform.

According to another embodiment of the invention said measurement means includes gate means for identifying points on the deconvolved waveform corresponding to a backwall or interface of the test member and a backwall of a film located on the test member, whereby the thickness of the film may be measured.

According to another embodiment of the invention said gate means includes a reference gate for identifying a peak of the deconvolved waveform which is associated with the backwall or interface of the test member, and a measurement gate for identifying a peak of the deconvolved waveform which is associated with a backwall of the film.

According to another embodiment of the invention the measurement gate floats relative to said reference gate.

DETAILED DESCRIPTION OF THE PREFERRED EMBODIMENT

The Wiener filter can be implemented by using an adaptive least-mean-square (LMS) algorithm, which greatly improves and simplifies ultrasonic measurement of thin films. According to the invention, an adaptive least-mean-square (LMS) implementation of a Wiener filter is used to deconvolve the ultrasonic waveforms in order to obtain approximate, but realizable, impulse signals for each separate backscattered event.

Figure 1:
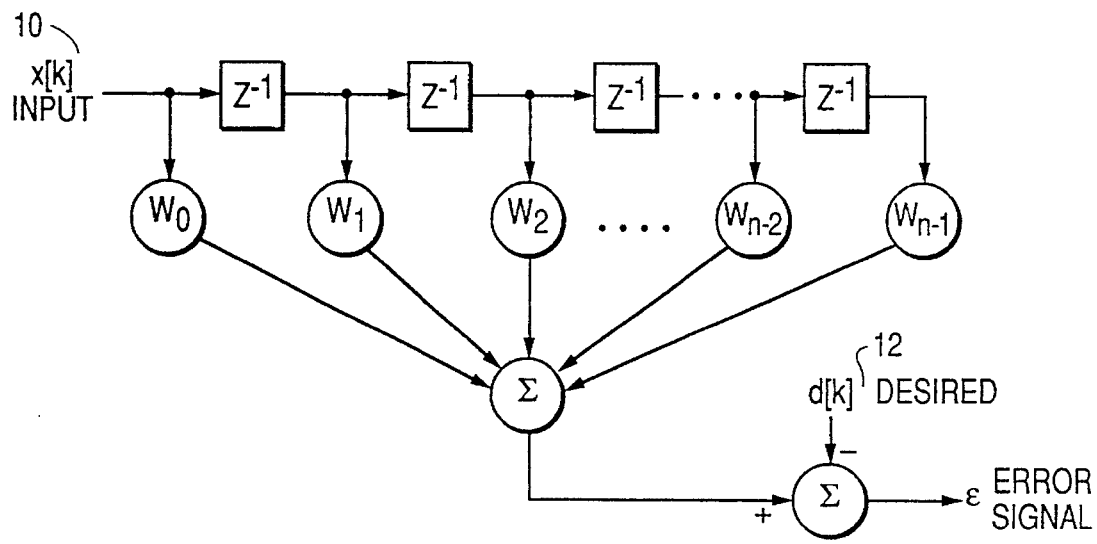
FIG. 1 is an illustration of the finite-impulse-response (FIR) structure of the filter according to one embodiment of the present invention.

The filter used is in the form of a tapped delay-line finite-impulse-response (FIR) filter, and is solved using Widrow's adaptive linear combiner. The formulation of the filter is shown in FIG. 1, as a single input linear combiner (non-recursive transversal filter) to solve for the FIR coefficients. As illustrated, this filter applies a linear transformation to an input 10 shown as x[k]. The estimation is linear in that the estimate of the signal y[k] obtained at an output 12 of the filter is linearly related to the samples of the process applied to the input 10.

The optimum weight vector, $W^*$, is that which results in the least mean square error. There are several ways to solve for the optimum weight vector. The direct and exact solution is to generate an input auto-correlation matrix, R, along with an output cross-correlation vector, P, of the desired signal and the input. The exact solution to the discrete-time Wiener-Hopf equation is provided in Equation (1):

$$W^* = R^{-1} P \qquad (1)$$

Figure 2:
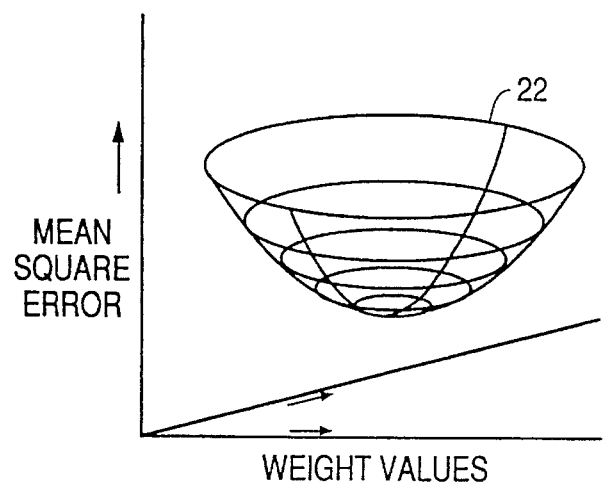
FIG. 2 is an illustration of the quadratic performance surface that is numerically searched to solve the filter of the present invention.

An alternate method is to use an adaptive least-mean-square LMS algorithm to converge to the optimum solution along a performance surface 22, as shown in FIG. 2. This technique has many advantages over the exact solution approach. Its simplicity and ease in programming is one of the major advantages. Another advantage is that predetermining expected-values, such as those required for the auto-correlation matrix R and cross-correlation vector P, are not required. In addition, taking the inverse of the R matrix is a computationally intensive task considering the number of weights that are typically required for this filter. The LMS algorithm is given by Equation (2):

$$W_{k+1} = W_k + 2\mu \epsilon_k X_k \qquad (2)$$

where, $$\epsilon_k = d[k] - X_k^T W_k \qquad (3)$$

The quantity $\mu$ is the convergence coefficient which determines the rate of convergence for the recursive equation and the minimum achievable mean-square error.

Figure 3:
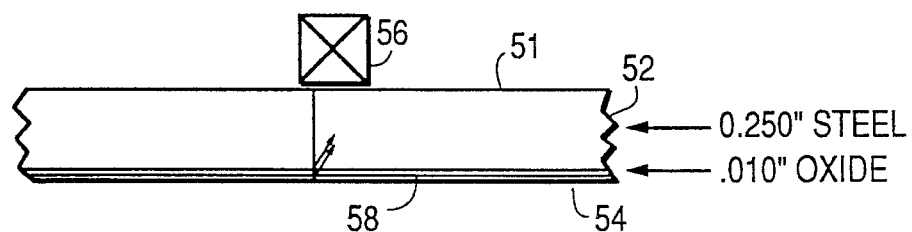
FIG. 3 is a representation of a test article configuration for the system to measure according to one embodiment of the present invention.

By implementing this technique according to the invention, it is possible to provide unambiguous, reliable, and accurate measurements of thin layers. For example, FIG. 3 shows a steel tube wall 52 having a thickness of 0.250" as measured from its surface 51 to its backwall 58. On the underside of the steel 52 is a thin layer oxide 54 having a thickness of 0.010". In order to obtain an accurate measurement of the oxide layer 54, a transducer 56 is used to introduce a sound impulse into a sample with known material characteristics. The amplitude of the sound impulse in the block 52 is then plotted as a function of time. Both the steel thickness and oxide can then be obtained from the resulting filtered waveform, as herein described.

Figure 4A:
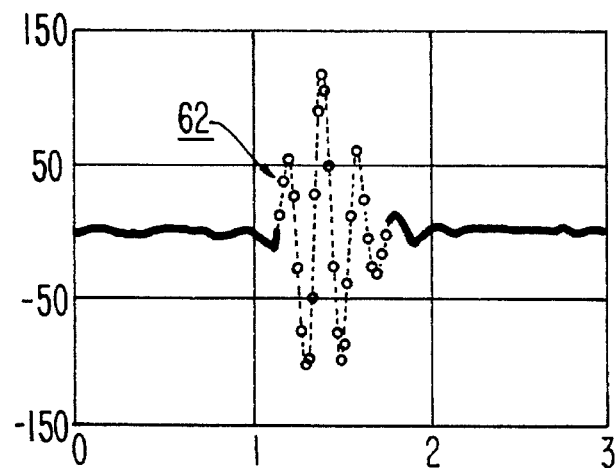
FIGS. 4A, 4B, and 4C are graphical representations of an unfiltered waveform; a synthesized desired waveform; and the resulting filtered response respectively obtained with an embodiment of the present invention.
Figure 4B:
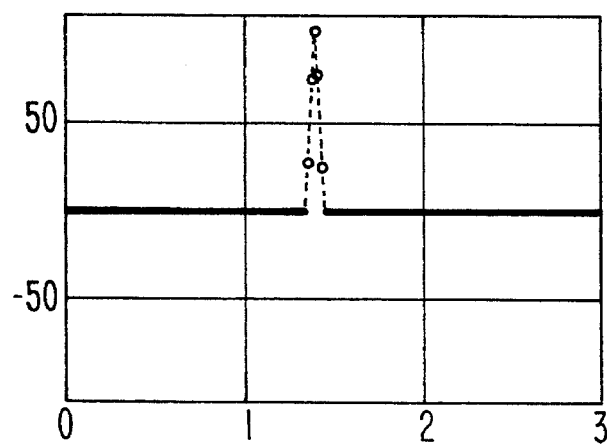
Figure 4C:
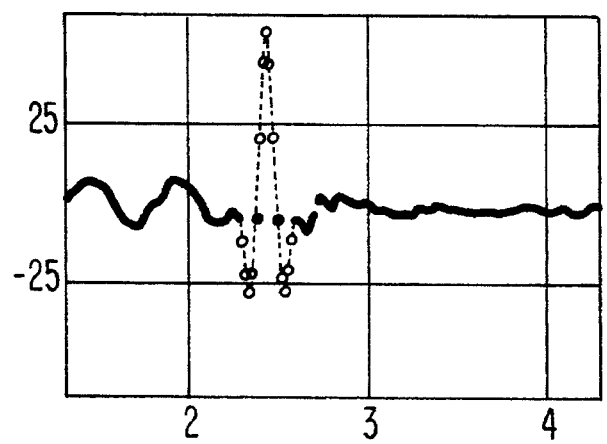

FIG. 4A shows a detected unprocessed waveform of a single event, e.g. a waveform obtained from a steel backwall with no oxide present. The obtained data points 62 provide a waveform which can be used to calibrate the system by solving for the filter coefficients and accurately determining the position of the backwall. FIG. 4B shows the desired response for filter adaptation according to the method described above. The resulting filtered waveform after adaptation (the Wiener filtered result) is shown in FIG. 4C. Once calibrated, the filtered waveforms are processed by identifying the appropriate peaks and measuring the time-of-flight between them to obtain wall and layer thickness measurements. As this example illustrates, because the filtered waveform has fewer peaks associated with it, it is simpler to evaluate. Furthermore, it provides greater resolution without the higher costs associated with high frequency measurement.

In a preferred embodiment of the invention, the above-described measurement technique is implemented with software and an associated detection apparatus. By incorporating software into the measuring system, it is possible to not only deconvolve the waveform, but also to automatically identify signal peaks and measure both wall and layer thickness.

Figure 5B:
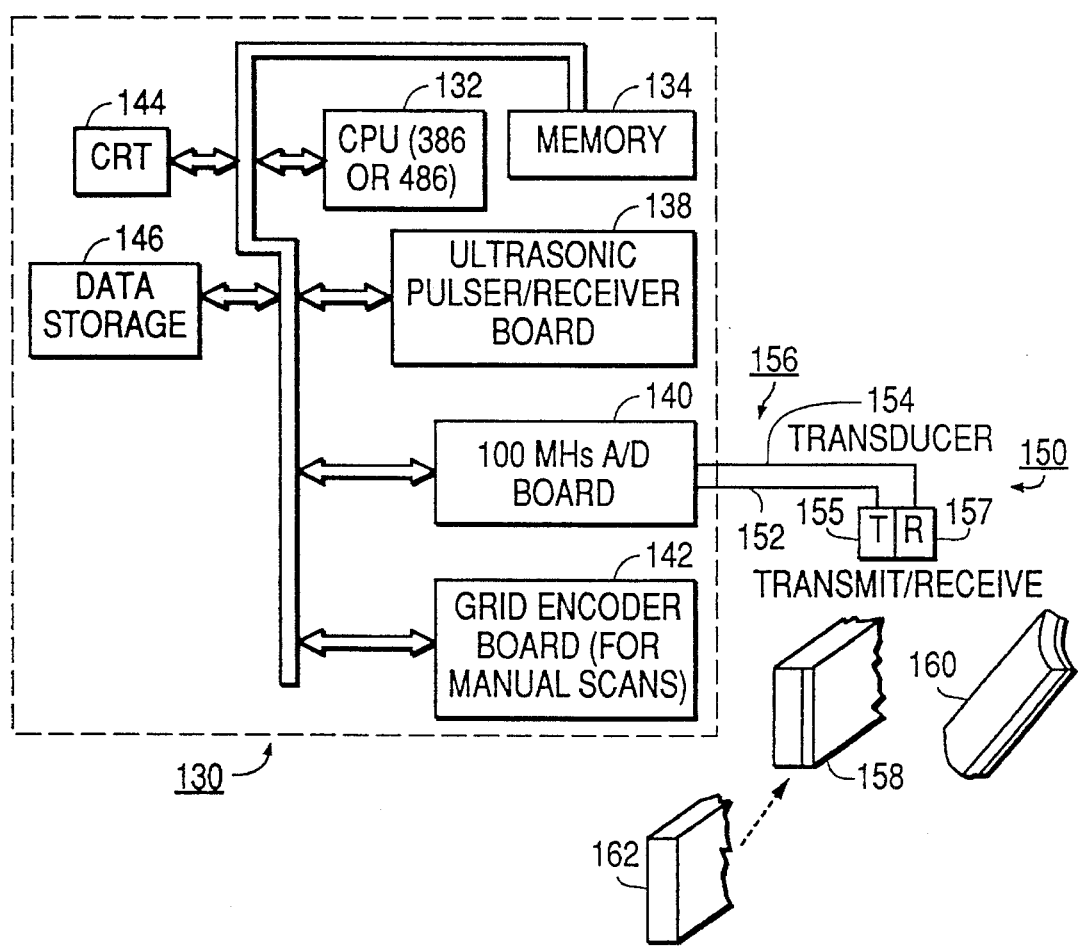
FIGS. 5A and 5B are diagrams of the standard Intraspect/ PC and its configuration according to the present invention.
Figure 5A:
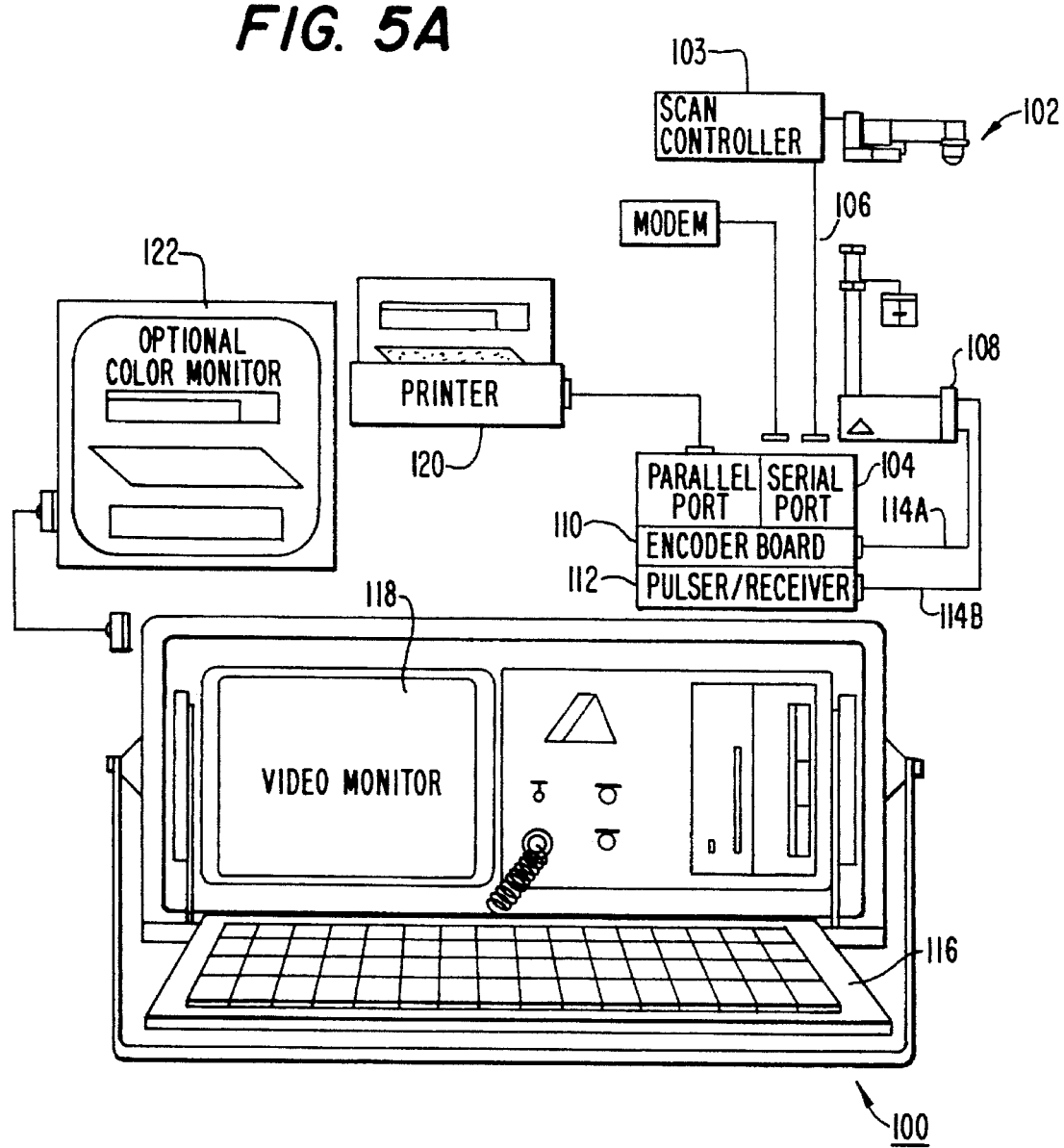

FIG. 5A illustrates one example of a measuring system according to the present invention. In FIG. 5A, a programmable microcomputer 100, e.g. a personal computer (PC), is operatively connected to a robotic scanner 102 through a serial port 104 and a cable 106. The robotic scanner 102 is mechanically controlled through a scan controller 103. Alternatively, the microcomputer 100 may be operatively connected to a manual scanner 108 via an encoder board 110, a pulser/receiver port 112, and cables 114A and 114B. In either case, a scanner is employed which has both a transducer for providing ultrasonic impulses to a sample and detection means for detecting the impulses after they have been introduced into the sample (not shown).

The PC 100 further has a user input device, such as a keyboard 116, as well as various user output devices, such as a video monitor 118, a printer 120 or a color monitor 122. These devices permit the operator to enter measurement parameters, control the measurement operation, and receive processed measurement data.

FIG. 5B shows in greater detail an example of such an embodiment. As represented, a PC 130 is operatively coupled to a transducer 150 via an umbilical cable 156 which includes a transmit cable 152 and a receive cable 154. The transducer 150 shown has both transmission means 155 for introducing an ultrasonic impulse, as well as detection means 157 for detecting the resulting ultrasonic waveform. The transducer is used to measure various objects, for example the portions of a vessel wall with an epoxy coating 158 or of a tube wall with an oxide layer 160. As explained below, it is used to verify velocity and gate settings with respect to a reference material, such as a reference block 162.

Furthermore, the PC 130 of this example includes a CPU 132 and an associated memory 134 connected via bus lines to an ultrasonic pulser/receiver board 138, a 100 MHz A/D board 140, and a grid encoder board 142. The CPU 132 is also coupled to a cathode ray tube display (CRT) 144 as well as data storage means 146, e.g. a disk storage device.

Using such an embodiment of the invention, deconvolution is begun by assuming an impulse (the desired response) to a known input (the ultrasonic response). Next, a transfer function is determined that, when convolved with the response, results in the assumed impulse. In this case, the transfer function is a long finite-impulse response (FIR) filter, typically requiring 16 to 128 taps to achieve acceptable results. Then, the several FIR coefficients that provide the best possible solution are solved. Once solved, the FIR coefficients are applied in an acceptable amount of time to the waveforms that require measurement. As explained in greater detail below, the PC may be programmed to perform these steps automatically.

Figure 6:
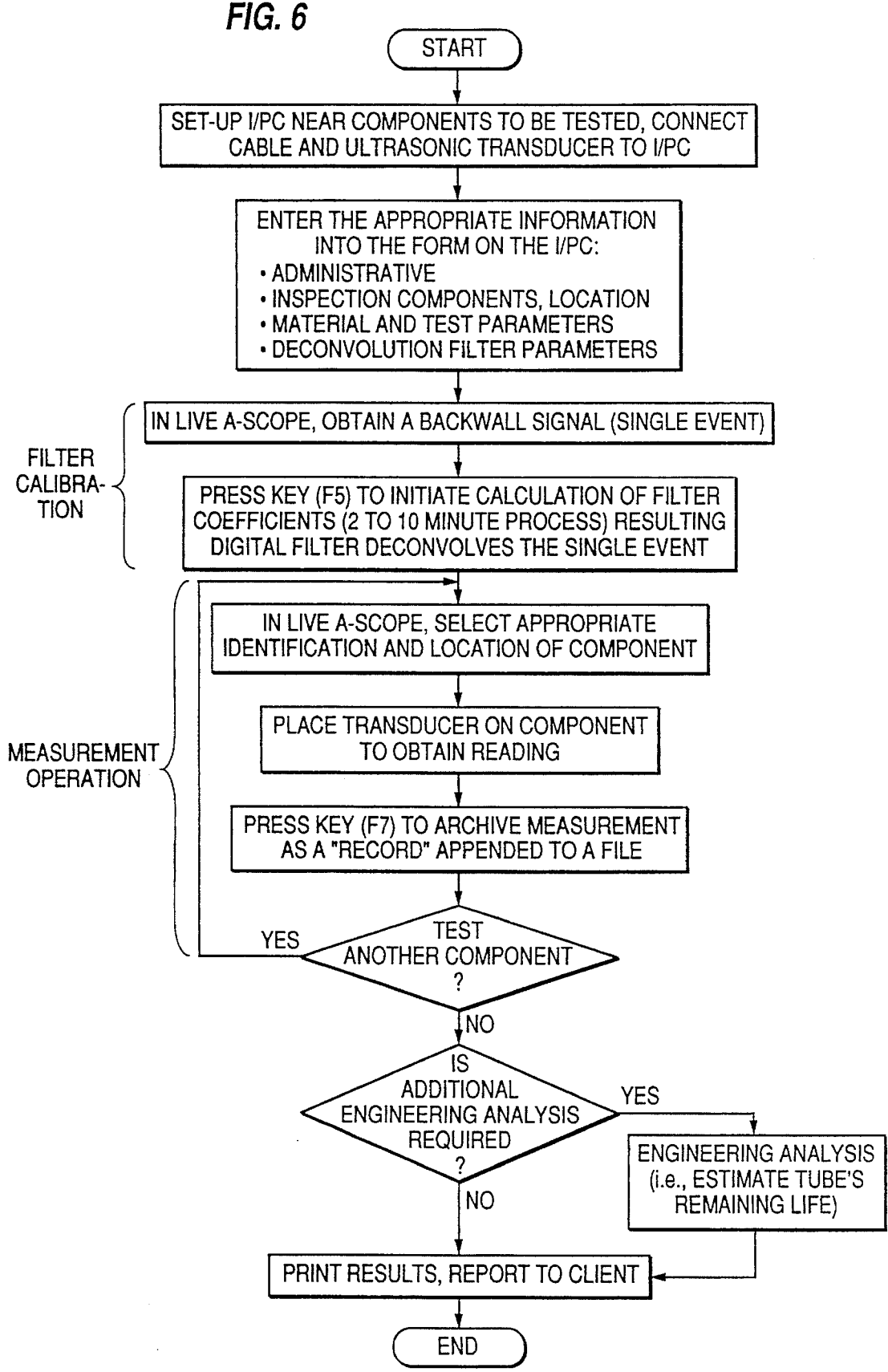
FIG. 6 is a flow chart describing the operation of an embodiment of the present invention.

In a typical operation of such a system, the PC can be programmed to operate under control of measurement software. An example of such an operation is shown in FIG. 6, discussed with reference to FIG. 5B. According to this flow chart, in order to commence a measurement operation, the operator first sets up the system. For example, the user would uncoil an umbilical cable, and connect the ultrasonic transducer to the PC 130. Uncoiling is necessary throughout operation of the transducer because the umbilical cable typically has an impedance which varies when coiled. Further, the umbilical cable should be properly terminated.

Next, the system is calibrated. This step includes the inputting of various parameters necessary in carrying out the measurement operation, as well as administrative data useful for referencing and identifying the measuring operation performed. This operation may be performed under the direction of a software routine (described as "the FORM" in FIG. 6).

Accordingly, the operator would set such variables associated with the measuring operation as: the sampling rate, the amplitude threshold, the velocity of sound in the test material, the pulse width, the pulse amplitude, damping, the gain tuning frequency, the transducer frequency, the velocity of sound in film to be measured, the calibration wall thickness, the number of taps, the number of Wiener iterations, the gain factor for the filtered waveform, the mu scale, the loop mu scale, and any other variables necessary for obtaining data and processing it as known in the art.

By way of illustration, the following is a sample of the calibration parameters used in conjunction with this embodiment of the invention:

| SAMPLE CALIBRATION PARAMETER MENU | | | |
|---|---|---|---|
| Formname | GENERAL INFORMATION SETSRP1 | | |
| Form Creation | Date | Time | |
| Exam | Date | Time | |
| Organization | | | |
| SITE | | | |
| Personnel | | | |
| ASME Code and revision | None | | |
| Specimen identifier | STATS | | |
| Type, configuration | Tube | | |
| Form, material | C. Steel | | |
| Surface condition | Sandblasted | | |
| Thickness, inches | 0.300 | | |
| Outer diameter, in. | 00.00 | | |
| Track diameter, in. | 00.00 | | |
| Reflector | Backwall | | |
| Software revision IPC386 B10 | Scan Controller SC5032 C | | Form REV o |
| | <MENU Page 1> | | |
| | CONTROL INFORMATION | | |
| Acquire | RF data | | |

SAMPLE CALIBRATION PARAMETER MENU -continued

| | | | | | |
|---|---|---|---|---|---|
| Manual scan mode | MinPeak | | | | |
| Sampling rate, MHz | 100.0 | | | | |
| Number wave avg. | 1 | | | | |
| Wave average type | RF | | | | |
| | A-gate | D-gate | C-gate | R-gate | M-gate |
| Delay usec | 20.00 | 26.40 | 20.00 | 21.00 | 1.00 |
| Width usec | 20.48 | 6.40 | 20.48 | 6.40 | 6.40 |
| Peak Type | | Maximum | First | Maximum | |
| Ampl. threshold % FSH | | 15 | 15 | 15 | |
| Interface gate? | | | | YES | |

<MENU Page 2>
SEARCH UNITS

| | | | |
|---|---|---|---|
| TX Manufacturer | KB | RX Manufacturer | KB |
| TX Model | DA-312 | RX Model | DA-312 |
| TX Serial Number | L13269 | RX Serial No. | L13269 |
| TX Frequency, MHz | 10.0 | RX Frequency, MHz | 10.0 |
| TX Inspect angdeg | 00.0 | RX Inspect angdeg | 00.0 |
| TX Mode | Longitudinal | RX Mode | Longitudinal |
| TX Wedge delay us | 5.56 | RX Wedge delay us | 5.56 |

| | |
|---|---|
| Inspection tech | Pitch-catch |
| Skew ang, deg | 0.0 |
| Veloc, mils/us | 232 |
| Trans OffX inch | 0.0 |
| Trans OffY inch | 0.0 |
| Trans OffZ inch | 0.0 |
| Couplant | Ultragel |

>MENU Page 3>
PULSER

| | |
|---|---|
| Manufacturer and model | Amdata PR35 |
| Serial number | 001 |
| Pulse width | 50 ns |
| Pulse amplitude | 200 volts |
| Damping | 50 ohms |

Receiver

| | |
|---|---|
| Manufacturer and model | Amdata PR35 |
| Serial number | 001 |
| Gain | 38.0 dB |
| Tuning frequency | 10.0 MHz |

<MENU Page 4>
DISPLAY PARAMETERS

| | | | |
|---|---|---|---|
| A-scan rectification | RF | | |
| A-scans with Peak/TOF display | YES | while scanning | NO |

-continued

| SAMPLE CALIBRATION PARAMETER MENU | |
|---|---|
| A-scan TOF mode | MP |
| A-scope display scale | 1:1 |
| DUAL calibration A-scope | YES |
| DUAL A-scope freerun | YES |
| DUAL A-scope filter | WIENER |
| B-scan rectification | FULL |
| Big B-scan | YES |
| B-scan Scaled | YES |
| C-scan scale | 1 |
| Max C-scan Pixel Size | 10 |
| C-scan horizontal label | Specimen X-axis |
| C-scan vertical label | Specimen Y-axis |
| C-scan display type | AMPLITUDE |

<MENU Page 5>
COMPONENT NAMES, MATERIAL SPECIFICATIONS

Component 1

| Component Name | 1 SH PanF | 2 SH PanR | 3 SH Plat | 4 SC Sper | 5 SH Pend |
|---|---|---|---|---|---|
| Component Name | 6 RH Pend | 7 | 8 | 9 | 10 |

Material 1

| Material | 1 | 2 | 3 | 4 | 5 |
|---|---|---|---|---|---|
| Outer Diameter | 0.0 | 0.0 | 0.0 | 0.0 | 0.0 |
| Wall Thickness | 0.0 | 0.0 | 0.0 | 0.0 | 0.0 |
| Material | 6 | 7 | 8 | 9 | 10 |
| Outer Diameter | 0.0 | 0.0 | 0.0 | 0.0 | 0.0 |
| Wall Thickness | 0.0 | 0.0 | 0.0 | 0.0 | 0.0 |

<MENU Page 6>
OXIDE THICKNESS MEASUREMENT PARAMETERS

| | Current | First | Last |
|---|---|---|---|
| Assembly | 1 | 1 | 300 |
| Tube | 1 | 1 | 99 |
| Location | 1 | 1 | 20 |

| | |
|---|---|
| AUTO sequencing | NO |
| Record number | 0 |
| Comment ID | 0 |
| Exam site ID | 1 |
| Transducer Frequency | 10.0 |
| Oxide velocity | 253 mils/usec |
| Cal. Wall Thick. | 0.310 inches |
| Maximum wave records | 1000 |

-continued

SAMPLE CALIBRATION PARAMETER MENU

<MENU Page 7>
OXIDE THICKNESS CALIBRATION PARAMETERS

| | |
|---|---|
| STATS enabled | YES |
| number of taps | 64 |
| Wiener iterations | 200 |
| Wiener scale | 2 |
| Initial mu scale | 0.10 |
| Loop mu scale | 0.988 |

<MENU Page 8>
REMARKS

Operator Comments:

1. Reading Taken onLeftSide of Tube.

2. Reading Taken on Right Side of Tube.

<MENU Page 9>

Once the PC 130 has been configured properly, the Wiener filter is calculated using a reference sample of material with a known thickness substantially similar to the test sample; of course, the reference sample must lack any oxide, epoxy or other layer, such as that to be measured. This operation is performed by placing the transducer on a reference sample, e.g. the tube 160 of FIG. 5B or a step wedge. The transducer is then used to obtain a backwall signal (a single event), and the Wiener coefficients are calculated using an appropriately programmed CPU.

More specifically, this calibration operation is performed by displaying a measured thickness of a reference sample of a known thickness and adjusting the system until the correct thickness is displayed. Once a peak signal is obtained, the CPU is used to calculate Wiener coefficients, which then may be conveniently stored as a binary file, for example. Normally, this will take between 5 to 10 minutes. The filtered (deconvolved) waveform is processed through a calibrated reference gate (R-gate) to identify the peak associated with the base material's backwall. This peak is used to accurately measure the base material wall thickness. In this way, the digital filter deconvolves the single event.

Once calibration has taken place, a sample, e.g. a vessel wall 158 or a tube wall 160, as in FIG. 5B, may be measured. The transducer 150 is placed on the test component and a thickness is calculated by the CPU 132 according to the programmed algorithm. Accordingly, the filtered waveform is further processed by a measurement gate (M-gate) used to determine the oxide or coating thickness. The peak found by the R-gate defines the beginning of the M-gate. Thus, the M-gate is floating and is determined dynamically by where a signal occurs in the R-gate. Typically, the maximum peak occurring in the M-gate identifies the thin layer backwall. Since the thin layer is typically a different material than the base, the appropriate velocity is applied to determine its thickness.

In a preferred embodiment, there are two options for visual display of the resulting filtered waveform. The first is a yellow display of the waveform in the R-gate, white display of the waveform in the M-gate operator with visual confirmation as to whether the gates have the appropriate ranges to capture relevant signal and avoid areas of excessive noise. The second display option is to use one color, magenta, to outline the time-of-flight measurement of the thin layer thickness. This provides the operator with the ability to quickly determine if the software has correctly identified the peaks, and thereby determine whether to record it as a valid measurement.

Continuing down the block diagram of FIG. 6, once an accurate measurement has been obtained, it may be archived in a manner well known in the art, e.g. saved as a archive file. The file may be either a binary file or a printable ASCII file, or both, and contain data associated with associated parameters as well as calculated data. If the operator so chooses, another test sample may then be measured with the calibrated system.

Once the last test sample is measured, the operator may then choose to perform further engineering analysis. This engineering analysis may consist of various manipulations of the measurement data, such as calculation of estimated life of the test sample. Once no further analysis is required, the system then may then print the results of the calculations in a manner known in the art.

Although a preferred embodiment has been described, other embodiments of the invention are possible. More specifically, the above disclosure makes apparent that the software used to implement the invention may be varied without departing from the scope of the invention. For example, it is possible to use the system to perform measurements based on 1st peak, maximum amplitude or 1st data point exceeding threshold. These features may be enabled, for example, through a MENU PAGE of the illustrative form described above. That is, a user may select one of these options when inputting control variables as described with respect to FIG. 6.

Further, the system can be programmed to apply a smoothing algorithm to a scan. According to this example, each colored data point within the peak of a scan would be replaced with a new pixel whose color is determined by the average of all peak values in the "neighborhood" of that data point, where the "neighborhood" of a data point is defined as all peak data within the scanned area that falls within a square centered on the current data point. The size of the square would be determined by the operator. In the event that the rectangle extends beyond the boundaries of the scanned area, only those point within the scanned area would be considered.

As mentioned above, there may be a second waveform which has two gates associated with it, a R-gate (reference gate) and a M-gate (measurement gate). Each of these gates have a peak type associated with them which can either be 'First' or 'Maximum'. Each of the gates also have their own amplitude threshold. Additionally, the M-gate delay (in uSecs) can entered into the form as either an absolute time (independent gate), or a relative time referenced from the R-gate peak TOF (interface gate). This may be accomplished, for example, by appropriately setting a form variable labeled "interface?" to 'YES'.

Moreover, the system may be enhanced by providing a dual scope. If such a dual display is enabled, each waveform acquired would have a second associated waveform displayed in a second display window. The second waveform, according to this example, may have two gates associated, the R-gate and the M-gate described above. Each of these gates may have a peak type associated with them and also independent amplitude threshold. Moreover, an M-gate delay may be entered as either an absolute time or a relative time related to the R-gate peak TOF. If the R-gate and the M-gate are used, the distance between the two peaks in the gates may be displayed under a second scope. As with other distance displays in such a scope, it can be displayed in either mils or uSecs. This display can be useful for measuring thickness, as well as calibrating material constants such as wedge delay and material velocity.

Other variations of these embodiments, for example variations of display options, user interfaces, and printing options, will be apparent to those skilled in the art.

By employing this invention, it is possible to obtain a high resolution measurement using lower frequencies. For example, measurement systems incorporating the invention have been used to accurately measure tube samples of 8 mils of oxide and 16 mils of oxide on their respective inside diameters. This resolution was possible at frequencies lower than prior art systems. Thus, the invention requires less preparation of test surfaces. This translates into cost savings. Costs are also reduced because more expensive components associated with high frequency measurement are no longer necessary.

The foregoing is a detailed description of the preferred embodiments. The scope of the invention, however, is not so limited. Various alternatives, such as modifications of the signal processing and display, as well as others, will be readily apparent to one of ordinary skill in the art. The invention is only limited by the claims appended hereto.

What is claimed is:

1. An apparatus for measuring films located on a test member comprising:

a transducer for providing an ultrasonic impulse to the test member;

detection means for detecting ultrasonic signals transferred through the test member, said detection means providing data signals indicative of said ultrasonic signals;

filtering means for providing a filtered time-based deconvolved waveform based on data signals provided by the detection means, said filtering means including processing means for applying a finite-impulse-response (FIR) filter to a waveform based on said data signals provided by the detection means; and measurement means for providing a measurement of the test member based on the deconvolved waveform, said measurement means including gate means for identifying portions of the filtered time-based deconvolved waveform corresponding to a backwall of the test member and a backwall of a film located on the test member, whereby the thickness of the film may be measured;

wherein said gate means includes a reference gate for identifying a portion of the filtered time-based deconvolved waveform corresponding to the backwall of the test member, and a measurement gate for identifying a portion of the filtered time-based deconvolved waveform corresponding to the backwall of the film.

2. The apparatus of claim 1 wherein said FIR filter is a Wiener filter and said processing means calculates Wiener filter coefficients associated with the waveform corresponding to the ultrasonic impulse.

3. The apparatus of claim 1 further comprising calibration means for calibrating the apparatus by use of a reference sample substantially similar to the testing sample.

4. The apparatus of claim 1 wherein said processing means includes a programmable CPU and memory means associated with the programmable CPU.

5. The apparatus of claim 1 further comprising display means for providing a visual display of the measurement of the test member.

6. The apparatus of claim 5 wherein said display means includes means for providing a visual display of the filtered time-based deconvolved waveform.

7. An apparatus for measuring films located on a test member comprising:

a transducer for providing an ultrasonic impulse to the test member;

detection means for detecting ultrasonic signals transferred through the test member, said detection means providing data signals indicative of said ultrasonic signals;

filtering means for providing a filtered time-based deconvolved waveform based on data signals provided by the detection means; and measurement means for providing a measurement of the test member based on the deconvolved waveform, said measurement means including gate means for identifying portions of the filtered time-based deconvolved waveform corresponding to a backwall of the test member and to a backwall of a film located on the test member, whereby the thickness of the film may be measured;

wherein said gate means includes a reference gate for identifying a portion of the filtered time-based deconvolved waveform which corresponds to the backwall of the test member, and a measurement gate for identifying a portion of the filtered time-based deconvolved waveform which is associated with a backwall of the film; and wherein said measurement gate floats relative to said reference gate.

8. A method of measuring films located on a test member comprising:

provivding an ultrasonic impulse to the test member with a transducer;

detecting ultrasonic signals transferred through the test member;

providing data signals indicative of said ultrasonic signals to a processing apparatus;

deconvolving in said processing apparatus a filtered time-based waveform based on data signals provided by the detection means; and displaying a measurement of the test member based on the filtered waveform;

wherein the step of deconvolving includes applying a finite-impulse-response (FIR) filter to a waveform based on said data signals provided by the detection means; and wherein said method further includes the steps of identifying a portion of the deconvolved waveform corresponding to a backwall of the test member, and identifying a portion of the deconvolved waveform corresponding to a backwall of a film located on the test member, whereby the thickness of the film may be measured; and wherein the step of identifying a portion of the deconvolved waveform corresponding to the backwall of the test member utilizes a reference gate, and wherein the step of identifying a portion of the deconvolved waveform corresponding to the backwall of the film utilizes a measurement gate.

9. The method of claim 8 wherein said FIR filter is a Wiener filter and wherein the step of applying a FIR filter included calculating Wiener filter coefficients associated with the waveform corresponding to the ultrasonic impulse.

10. The method of claim 8 further comprising the step of calibrating the transducer and the processing apparatus by use of a reference sample substantially similar to the testing sample.

11. The method of claim 8 wherein the step of applying a FIR filter is accomplished with a programmable CPU and memory means associated with the programmable CPU.

12. The method of claim 8 wherein the step of displaying includes providing a visual display of the measurement of the test member.

13. The method of claim 12 further comprising the step of providing a visual display of the deconvolved waveform.

14. A method of measuring films located on a test member comprising:

providing an ultrasonic impulse to the test member with a transducer;

detecting ultrasonic signals transferred through the test member;

providing data signals indicative of said ultrasonic signals to a processing apparatus;

deconvolving in said processing apparatus a filtered time-based waveform based on data signals provided by the detection means; and displaying a measurement of the test member based on the filtered waveform;

wherein said method further includes the steps of identifying a portion of the deconvolved waveform corresponding to a backwall of the test member, and identifying a portion of the deconvolved waveform corresponding to a backwall of a film located on the test member, whereby the thickness of the film may be measured;

wherein the step of identifying a portion of the deconvolved waveform corresponding to the backwall of the test member utilizes a reference gate, and wherein the step of identifying a peak of the deconvolved waveform corresponding to the backwall of the film utilizes a measurement gate; and wherein said measurement gate floats relative to said reference gate.

15. The apparatus of claim 7 wherein said filtering means include processing means for applying a finite-impulse-response (FIR) filter to a waveform based on said data signals provided by the detection means.

16. The apparatus of claim 15 wherein said FIR filter is a Wiener filter and said processing means calculates Wiener filter coefficients associated with the waveform corresponding to the ultrasonic impulse.

17. The method of claim 14 wherein the step of deconvolving includes applying a finite-impulse-response (FIR) filter to a waveform based on said data signals provided by the detection means.

18. The method of claim 17 wherein said FIR filter is a Wiener filter and wherein the step of applying a FIR filter included calculating Wiener filter coefficients associated with the waveform corresponding to the ultrasonic impulse.

* * * * *